(12) United States Patent
Tsenkova et al.

(10) Patent No.: US 6,748,251 B2
(45) Date of Patent: *Jun. 8, 2004

(54) METHOD AND APPARATUS FOR DETECTING MASTITIS BY USING VISUAL LIGHT AND/OR NEAR INFRARED LIGHTS (75) Inventors: Roumiana Tsenkova, Kobe (JP); Koichi Murayama, Sennan (JP)

(73) Assignee: Japan, as represented by President of Kobe University, Kobe (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/980,213
(22) PCT Filed: Mar. 14, 2001
(86) PCT No.: PCT/JP01/02018
§ 371 (c)(1), (2), (4) Date: May 28, 2002
(87) PCT Pub. No.: WO01/75421
PCT Pub. Date: Oct. 11, 2001

(65) Prior Publication Data
US 2002/0183600 A1 Dec. 5, 2002

(51) Int. Cl.[7] .................... A61B 5/00; A01J 7/00
(52) U.S. Cl. .................. 600/310; 600/309; 600/473; 600/476; 119/14.14
(58) Field of Search ................. 600/309, 310, 600/473, 476; 119/14.14, 14.07

(56) References Cited
U.S. PATENT DOCUMENTS

| | | | | |
|---|---|---|---|---|
| 4,385,590 A | * | 5/1983 | Mortensen | 119/14.01 |
| 5,520,787 A | * | 5/1996 | Hanagan et al. | 204/403.14 |
| 5,596,992 A | * | 1/1997 | Haaland et al. | 600/473 |
| 5,830,133 A | * | 11/1998 | Osten et al. | 600/322 |

FOREIGN PATENT DOCUMENTS

| | | |
|---|---|---|
| HU | 172951 B | 7/1978 |
| JP | 4-47254 | 2/1992 |
| JP | 7-306139 | 11/1995 |
| JP | 2000-146832 | 5/2000 |
| RU | 97118363 | 8/1999 |
| SU | 1832008 | 8/1993 |

OTHER PUBLICATIONS

"Reflectance/Transmittance Systems", Advertising Brochure, Labsphere, Inc., pp. 72–74, 1994–1995, North Sutton, NH, USA.

K. Murayama et al, "Raw Milk Near Infrared Spectra for Mastitis Diagnosis", Dai 16 Kai Hihaki Keisoku Symposium Koen Yoshihuu (Japan) Shadan Hojin Nippon Shokuhin Kagaku Kogakukaied., Nov. 8, 2000, pp. 184–189.

R.N. Tsenkova et al, "Near–Infrared Spectroscopy of Individual Cow Milk as a Means for Automated Monitoring of Udder Health and Milk Quality", Proc. 3rd. Int. Diary Housing Conf., (1994) pp. 82–91.

(List continued on next page.)

Primary Examiner—Max F. Hindenburg
Assistant Examiner—Matthew J Kremer
(74) Attorney, Agent, or Firm—Burns, Doane, Swecker & Mathis, LLP (57) ABSTRACT A method for diagnosing mastitis of cows, includes the steps of (1) irradiating visual light rays and/or near infrared rays in a wavelength range of 400 to 2500 nm into urine, raw milk or a mammary gland of a cow, (2) detecting an intensity of transmitted light rays, reflected light rays or transmitted and reflected light rays from said urine, raw milk or mammary gland, and (3) effecting multivariate regression analysis, and (4) diagnosing the presence of the mastitis of the cow.

11 Claims, 9 Drawing Sheets-

OTHER PUBLICATIONS

R. Tsenkova, "Near Infrared Spectroscopy: A Uniform Measuring Technology For A Sustainable Diary Production System", J. Near. Infrared Spectroscopy, No. 6, (1998), pp. A45–A51.

Prospects for Automatic Milking, (1992), EAAP publ. No. 65.

R. Tsenkova et al, "Near Infrared Spectroscopy for Biomonitoring: Cow Milk Composition Measurement in a Spectral Region from 1,100 to 2,400 Nanometers[1]", J. Anim. Sci., vol. 78, No. 3, Mar. 31, 2000, pp. 515–522.

Optronics (Japan), No. 205, (1999), pp. 211–214, (especially, Chapter 2.2).

* cited by examiner

FIG. 4
VIS-NIR Spectra

Relationship between logSCC of urines determined in laboratory and values presumed by NIR spectra

METHOD AND APPARATUS FOR DETECTING MASTITIS BY USING VISUAL LIGHT AND/OR NEAR INFRARED LIGHTS

TECHNICAL FIELD TO WHICH THE INVENTION PERTAINS

The present invention relates to a method and an apparatus for diagnosing the mastitis based on visual light and/or near infrared spectra from urine, raw milk or mammary gland of cows.

PRIOR ART TECHNIQUE

The number of somatic cells in raw milk is an important factor for the mastitis diagnosis. Heretofore, a direct microscopy method, a CMT modified method, and a fluorometry have been used for measuring the number of the somatic cells.

At present, a fluorometrical type somatic cell counter (Fossomatic) is used to measure the number of the somatic cells in the raw milk. This apparatus can calculate and display the number of the somatic cells per 1 ml through mixing a buffer solution and a dying liquid (ethidium bromide solution) to the raw milk, fluorescently staining cell nuclei of the somatic cells, scatteredly applying the resulting mixture to a peripheral portion of a disc continuously rotated with use of a microsyringe, and automatically measuring the number of the somatic cells with the fluorescent microscope.

In Japan, it is prescribed that if the number of the somatic cells is 300,000 or more per 1 ml in the measurement of the raw milk with the fluorometrical type somatic cell counter (Fossomatic), the cow is judged to suffer the mastitis, and prohibited from being milked.

PROBLEMS TO BE SOLVED BY THE INVENTION

However, the conventional mastitis diagnosis method based on the measurement of the somatic cells with the fluorometrical type somatic cell counter has various problems to be solved, in that (1) the raw milk taken needs to be subjected to preliminary treatment with the addition of chemicals such as the buffer solution and the dying liquid; (2) the raw milk sample cannot be measured in a non-destructive manner (3) the raw material is likely to be influenced with another substance; (4) the prices of the chemicals are high, which is disadvantageous from the standpoint of the cost performance; and (5) skillful technical [method is required to handle the apparatus and the sample.

It is an object of the present invention to provide a measuring method and apparatus and a judgment method therefore, which perform the diagnosis of the mastitis at a high precision in a short time through the optical measurement of the visual light and/or near infrared spectra from urine, raw milk or a mammary gland of a cow.

MEASURES TO SOLVE THE PROBLEMS

The present invention relates to the method for diagnosing mastitis of cows, comprising the steps of irradiating visual light rays and/or near infrared rays in a wavelength range of 400 to 2500 nm into urine, raw milk or a mammary gland of a cow, detecting an intensity of transmitted light rays, reflected light rays or transmitted and reflected light rays from said urine, raw milk or mammary gland, effecting multivariate regression analysis, and diagnosing the presence of the mastitis of the cow. With respect to the visual light rays and/or the near infrared rays to be used for the detection, those in a wavelength judged effective for the diagnosis of the mastitis are selected.

According to the present invention, the absorbance, which varies depending upon the number of the somatic cells in urine, raw milk or mammary gland, can be determined by detecting the intensity of the transmitted light rays, reflected light rays or transmitted and reflected light rays from the urine, raw milk or mammary gland of the cow. Thus, the mastitis of the cow can be diagnosed by performing the multivariate regression analysis, and diagnosing the presence of the mastitis of the cow. Therefore, it is no need to effect the conventionally troublesome pretreatments, to use expensive chemicals, etc. and to skillfully handling samples. The intensity of the light rays, etc. reflected from the mammary gland means the intensity of the reflected light rays, etc. from the tissues of the living body including mammal cells. It is considered that mammary gland cells (including the raw milk) and the living tissues are milky and cuvette, respectively, in the mammary gland. As to the measurement of the transmitted light rays, for example, the incident light rays are applied to a one right side of the mammary gland through an optical fiber, and the transmitted light rays (on a side of the detector) are measured through another optical fiber applied to an another left side of the mammary gland, while the optical fiber is applied to a left side. The light rays in the near infrared range pass an even thick path in mammary gland depending upon the wavelength range.

The wavelength of the visual light rays and the near infrared rays to be used for the diagnosis of the mastitis in the present invention ranges from 400 nm to 2500 nm. If the visual light rays and the infrared rays in a range of 400 nm to 1100 nm are used, a silicon light detector is used. If the near infrared rays in the wavelength range of 700 nm to 2500 nm are used, a light detector of such as PbSe, InGaAs or GaAs is used.

Since the visual light rays and the near infrared ray in the range of 400 nm to 700 nm have noises it is preferable to use the near infrared rays in the range of 700 to 2500 nm among the above-mentioned wavelength range of the visual light rays and the near infrared rays. Further, since the raw milk contains various ingredients such as water, proteins, fat, carbohydrates, minerals, etc. and light rays are absorbed principally by water as the main ingredient at various wavelength regions, it may be feared that such will interrupt the measurement of the near infrared spectra. However, the water-related influence is smaller in the wavelength region of 700 to 2500 nm as compared with those in the other wavelength region. In the wavelength region of 1100 to 2500 nm, changes in the absorbance of the somatic cells in the urine, raw milk or mammary gland appear as first harmonic tone or combination tone of molecular vibrations. Therefore, the measurement is preferably made with the near infrared rays in the wavelength range of 1100 nm to 2500 nm, which enables measurement of the somatic cells in the urine, raw milk or mammary gland in a short time.

Moreover, since the intensity of the light absorption in the urine, raw milk or mammary gland is relatively small in the wavelength region of the infrared rays, the thickness of the sample can be ensured at a few or several mm in the measurement of the transmitted light rays or the transmitted and reflected light rays. Therefore, it is easy to handle and set a sample container.

The mastitis of the cows can be readily diagnosed at high precision through the optical measurement of the urine, raw milk or mammary gland and the data processing based on the multivariate regression. The method for the diagnosis of the cow mastitis, which uses the optical measurement values for the urine, raw milk or mammary gland and data processing based on the multivariate regression analysis, will be explained later.

The present invention is characterized in that the incident light rays, transmitted light rays, reflected light rays or transmitted and reflected light rays from the urine, raw milk or mammary gland in the optical measurement is scanned over the wavelengths by using a spectroscope, and the multivariate regression analysis is applied to the spectroscopic spectra obtained.

According to the present invention, since substantially continuous spectroscopy spectra having a high wavelength resolution can be obtained through scanning over the wavelengths with use of the spectroscope, such a large amount of data as required for the data analysis can be obtained. For example, if the scanning is effected in the wavelength region of 1100 to 2500 nm at a wavelength resolution of 2 nm, 701 data points can be taken in per one scanning, resulting in enhanced precision of the data analysis.

The present invention also relates to the apparatus for diagnosing mastitis of cows, comprising: (1) a near infrared ray generator for generating visual light rays and/or near infrared rays in a wavelength range of 400 nm to 2500 nm; (2) an optical system for introducing the visual light rays and/or near infrared rays into urine, raw milk or a mammary gland of a cow; (3) a detector for detecting an intensity of transmitted light rays, reflected light rays or transmitted and reflected light rays from said urine, raw milk or mammary gland; (4) and a data processor for receiving signals from said detector, and effecting multivariate regression analysis to diagnose the presence of the mastitis in cow.

The mastitis diagnosis apparatus according to the present invention preferably further comprises an optical fiber for leading visual light rays and/or near infrared rays from said urine, raw milk or a mammary gland of the cow to the light detector, so that the intensity of transmitted light rays, reflected light rays or transmitted and reflected light rays from said urine, raw milk or mammary gland is detected with said detector through the optical fiber.

The utilization of the optical fiber can provide a portable, compact mastitis diagnosis apparatus.

The cow mastitis-diagnosing apparatus preferably further comprises a feeder for introducing said raw milk into a raw milk sample container via an in-line or at line.

The provision of the feeder for introducing said raw milk into the sample container via an in-line or at line enables the continuous measurement of the visual light rays and/or near infrared rays with the lapse of time.

The cow mastitis-diagnosing apparatus further comprises a sample container for holding the raw milk, and a temperature controller for stabilizing the milk inside the sample container to a given temperature.

Stabilization of the temperature of the raw milk in the sample container can prevent variations in absorbance of the raw milk due to temperature, which can enhance the precision in the diagnosis of the mastitis. When the mammary gland is measured to diagnose the mastitis, the mammary gland is held with a milking machine, and the temperature is controlled in the same way as mentioned above, if necessary.

EMBODIMENTS OF WORKING THE PRESENT INVENTION

The mastitis-diagnosing apparatus according to the present invention will be explained with reference to FIG. 1.

Figure 1:
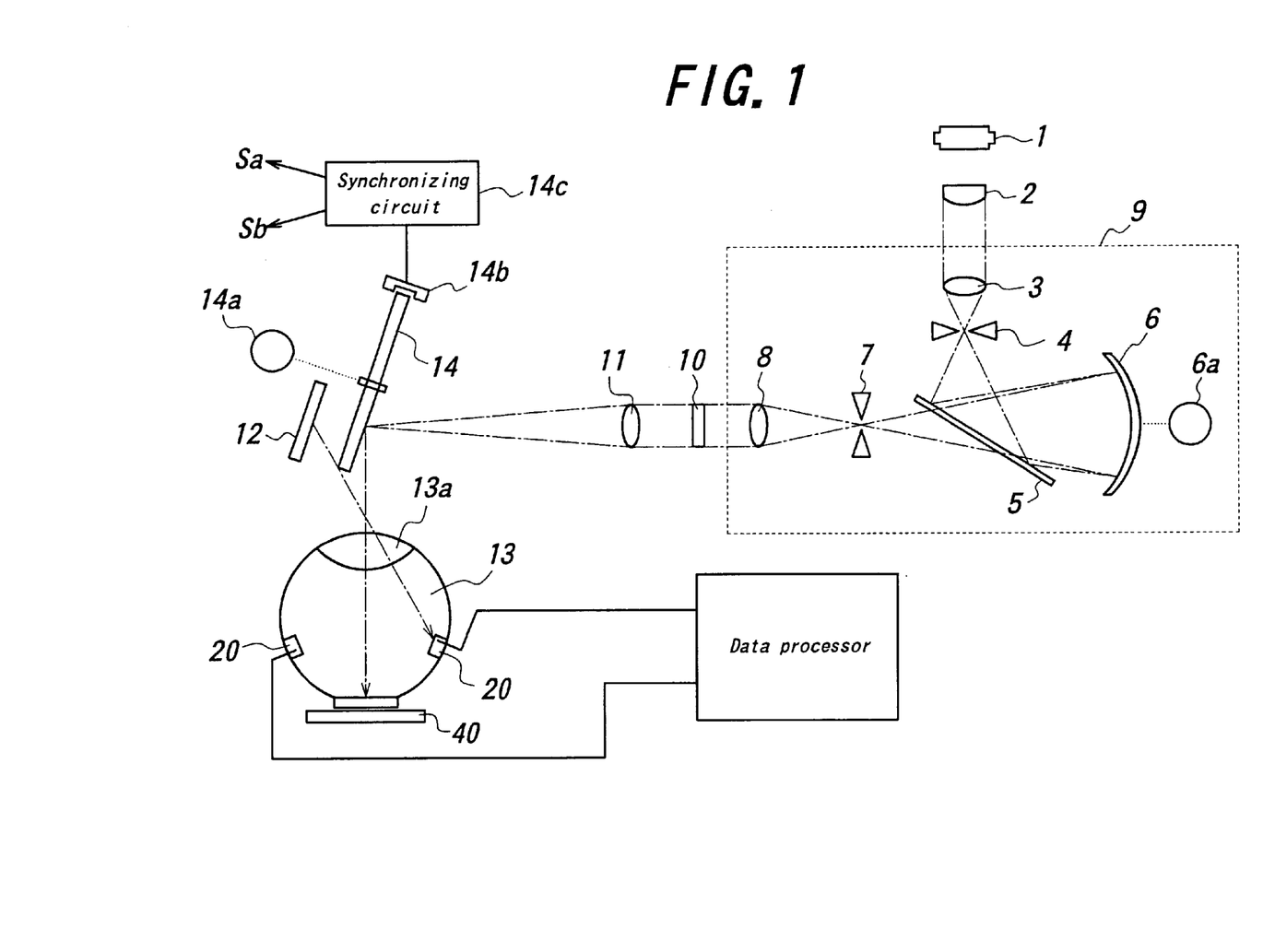
FIG. 1 is a construction view of a raw milk spectra-measuring apparatus as one embodiment of the present invention.

FIG. 1 is a construction view of a raw milk spectra-measuring apparatus as one embodiment of the present invention. As viewed in the light-progressing direction, this apparatus comprises a light source for generating measuring light rays, a lens 2 for making light rays from the light source 1 in parallel to one another, a spectroscope 9 for taking out desired light rays through separating the light rays from the light source 1, a filter 10 for cutting off a high light portion of the light rays emitted from the spectroscope, a lens 11 for collecting the separated light rays, a reflection mirror 12 for reflecting the light rays from the lens 11, a light chopper 14 interposed between the lens 11 and the reflection mirror 12, an integrating sphere 132 formed of a light-diffusing material, a sample holder 40 for holding a sample, etc.

The light source 1 is constituted by a tungsten halogen lamp or the like, which generates a wide wavelength range of the light rays including near infrared rays. The spectroscope 9 comprises a lens 3 for collecting the incident light rays, a slit 4 for regulating the size and the amount of the light ray flux, a reflection mirror 5 for reflecting the light rays having passed the slit 4, a diffraction grating 6 having a curved surface, a motor 6a for controlling the diffraction angle of the diffraction grating 6, a slit 7 for passing only a desired light portion among the light rays diffracted at the diffraction grating 6, a light-emitting lens 8 for emitting the diffracted light rays in parallel to one another, etc. Only the light rays with the desired wavelength can be selectively taken out by the angular controlling with the motor 6a.

The light chopper 14 is designed in the form of a rotary disc in which light-reflecting sections and light-permeating sections are alternatively arranged, and the light rays coming from the lens 11 is periodically reflected or passed by rotating the optical chopper 14 through driving a motor 14a. A chopper sensor 14b detects the rotary phase of the light chopper 14, and a synchronizing circuit 14c outputs synchronizing signals Sa and Sb indicative of the reflected and passing states for the light rays from the lens 11, respectively, based on the signals from the chopper sensor 14b.

The integrating sphere 13 comprises an incident light window 13a opened upwardly, a light-emitting window 13b opened downwardly, and plural light detectors 20 for converting amounts of received light rays to electric signals. The integrating sphere 13 functions to diffuse the light rays entering the sphere to reduce measurement errors. The detector 20 is constituted by PbS or the like, which has a sensitivity in the near infrared ray region. The sample holder 40 is arranged near the light-emitting window 13b.

If the light rays, which are separated by the spectroscope 9, are reflected with the light chopper 14, the light rays come into the sample holder 40 as it is through the integrating sphere 13 via the incident light window 13a. As a result, return light rays diffuse in the integrating sphere 13, so that a part of the light rays are received with the light detectors 20. On the other hand, if the light rays separated with the spectroscope 9 passes the light chopper 14, the light rays are reflected with the reflection mirror 12, so that the light rays enter obliquely into the integrating sphere 13 via the incident light window 13a. Consequently, the light rays are diffused without reaching the sample, and a part of that light rays are received by the light detector 20. The above operation of the chopper takes out signals influenced with the sample and those not influenced with the sample.

Figure 2:
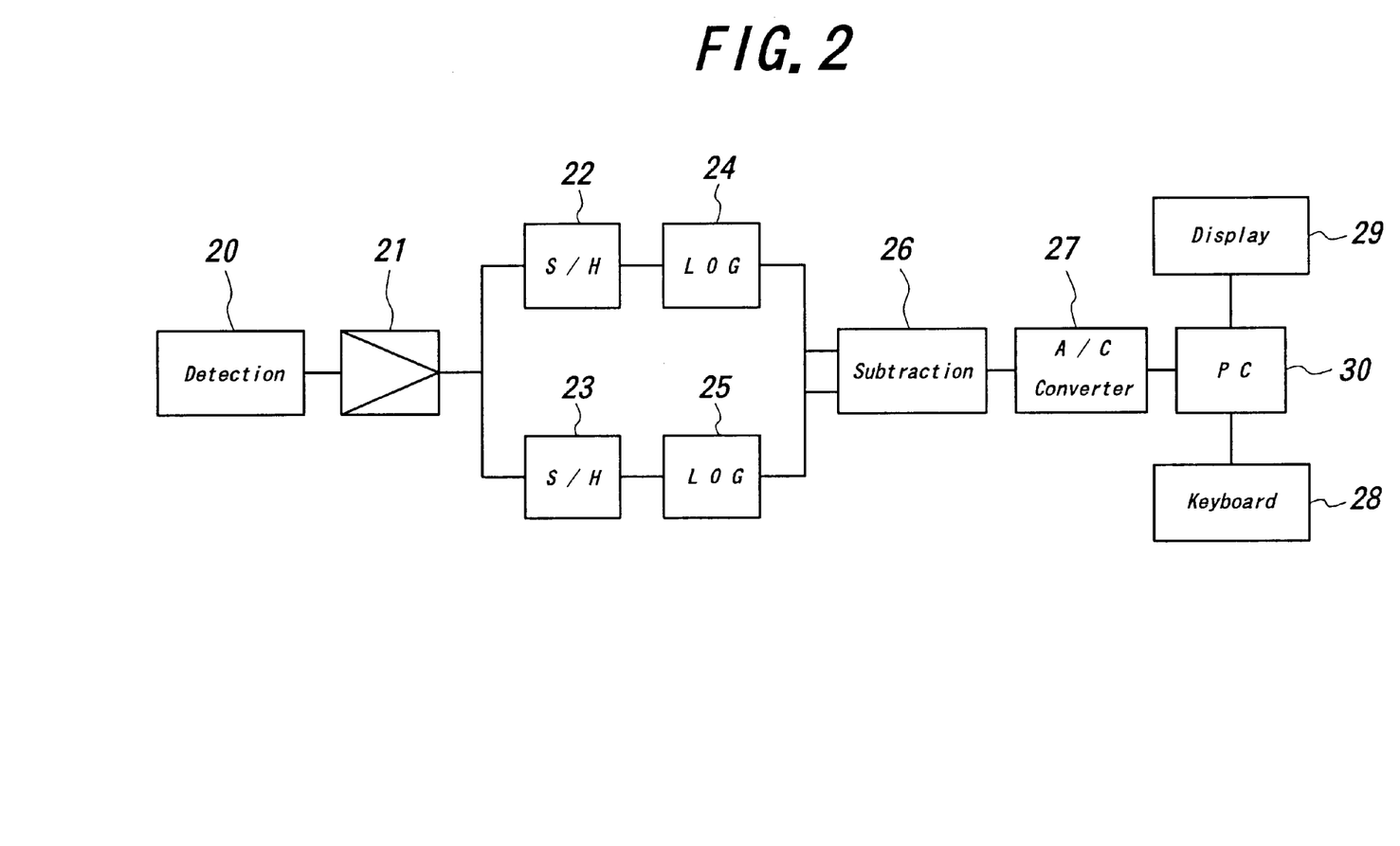
FIG. 2 is a block diagram constituting an example of an electric construction of the raw milk spectra-measuring apparatus.

FIG. 2 is an example of a block diagram showing an electric construction of the data processor of the raw milk spectra-measuring apparatus. Detection signals from light detectors 20 are amplified with an amplifier 21, and inputted to a sample holding circuit 22 for sampling with synchronizing signals Sa and a sample holding circuit 23 for sampling with synchronizing signals Sb. The sample holding circuit 22 holds a signal voltage only during a sampling time period when the light rays enter the sample from the spectroscope 9, whereas the sample holding circuit 23 holds the electric signals only during the sampling time period when the light rays do not enter the sample from the spectroscope 9. Then, output signals from the sample holding circuits 22 and 23 are logarithmically converted with logarithmically converting circuits 24, 25, respectively, which are subjected to subtraction between them in a subtraction circuit 26. Disturbance components can be removed through detection in synchronization with the light chopper 14.

Output signals from the subtraction circuit are quantized with an AD (analogue/digital) converter 27, which is led into a personal computer (PC) 30 in which various programs are installed to effect data processing according to the multivariate regression method. To the PC 30 are connected a keyboard 28 for inputting data, a display 29 for displaying the data, etc.

Figure 3:
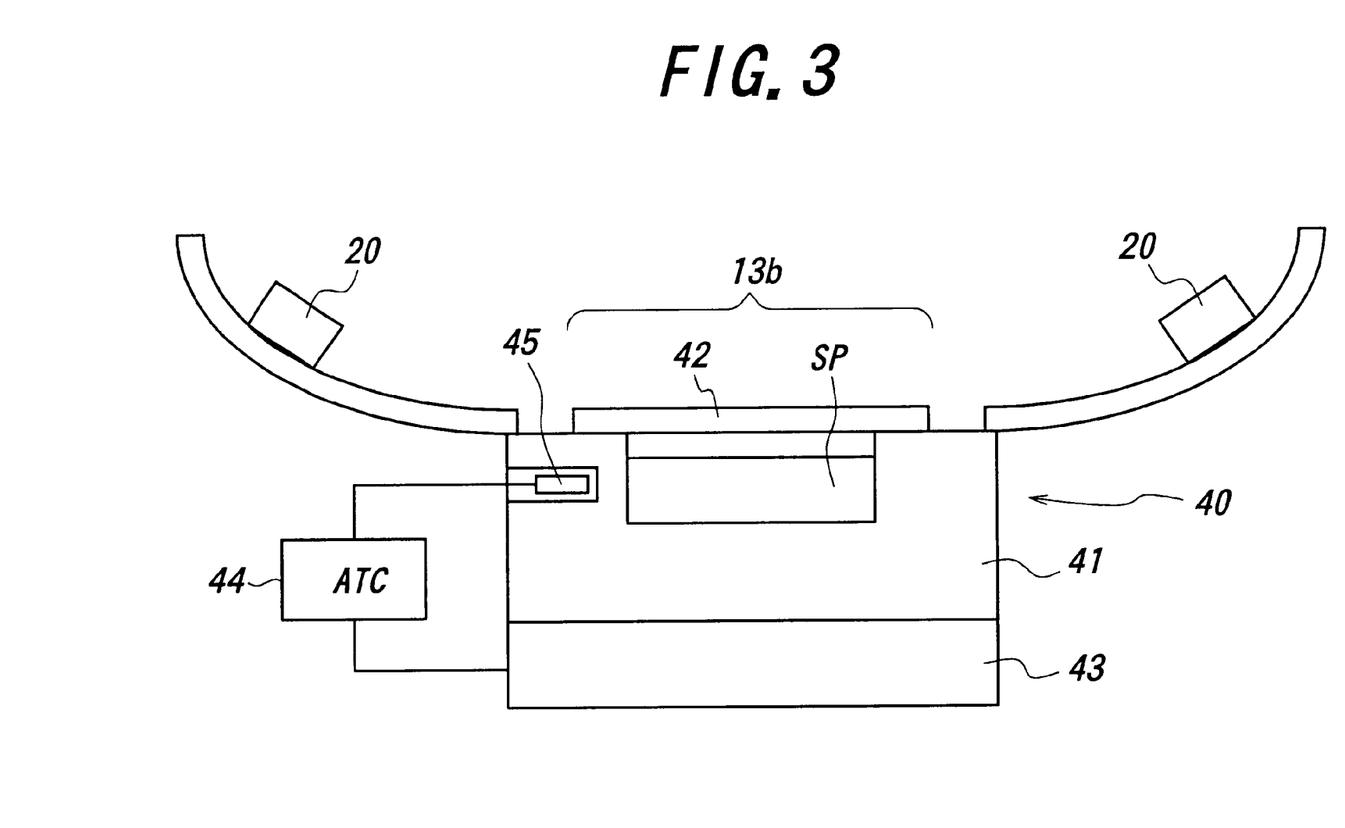
FIG. 3 is a sectional view of a sample holder 40.

FIG. 3 is a sectional view showing the construction of a sample holder 40. This sample holder 40 fits to the configuration of the light-emitting window 13b of the integrating sphere 13. The sample holder, which is made of a heat-conductive material such as aluminum, comprises a sample container 41 for holding a liquid sample SP such as a raw milk, a transparent cover glass plate 42 for covering an opening of the sample container 41, a Peltier element for heating or cooling the sample container 41, a temperature sensor 45 for controlling the temperature of the sample container 41, a temperature-controlling circuit 44 for stabilizing the temperature of the sample SP by driving the Peltier element based on temperature signals from the temperature sensor 45, etc.

When the light rays reflected from the light chopper 14 enter the sample SP via the cover glass plate 42, they return into the integrating sphere 13 again after being attenuated and scattered depending upon the absorption spectra of the sample SP. Consequently, a part of the returned light rays are received by the light detector 210 where they are converted to electric signals.

Since the absorbance of the raw milk is sensitive to changes in temperature and less influence of fat in the raw milk has to be achieved, significance of the measurement may be lost if the measurement environmental temperature changes every measurement. Thus, according to this embodiment, the temperature of the sample SP is stabilized by the temperature feed-back system constituted by the temperature sensor 45, the temperature-controlling circuit 44 and the Peltier element 43, thereby enhancing the measuring precision.

Figure 4:
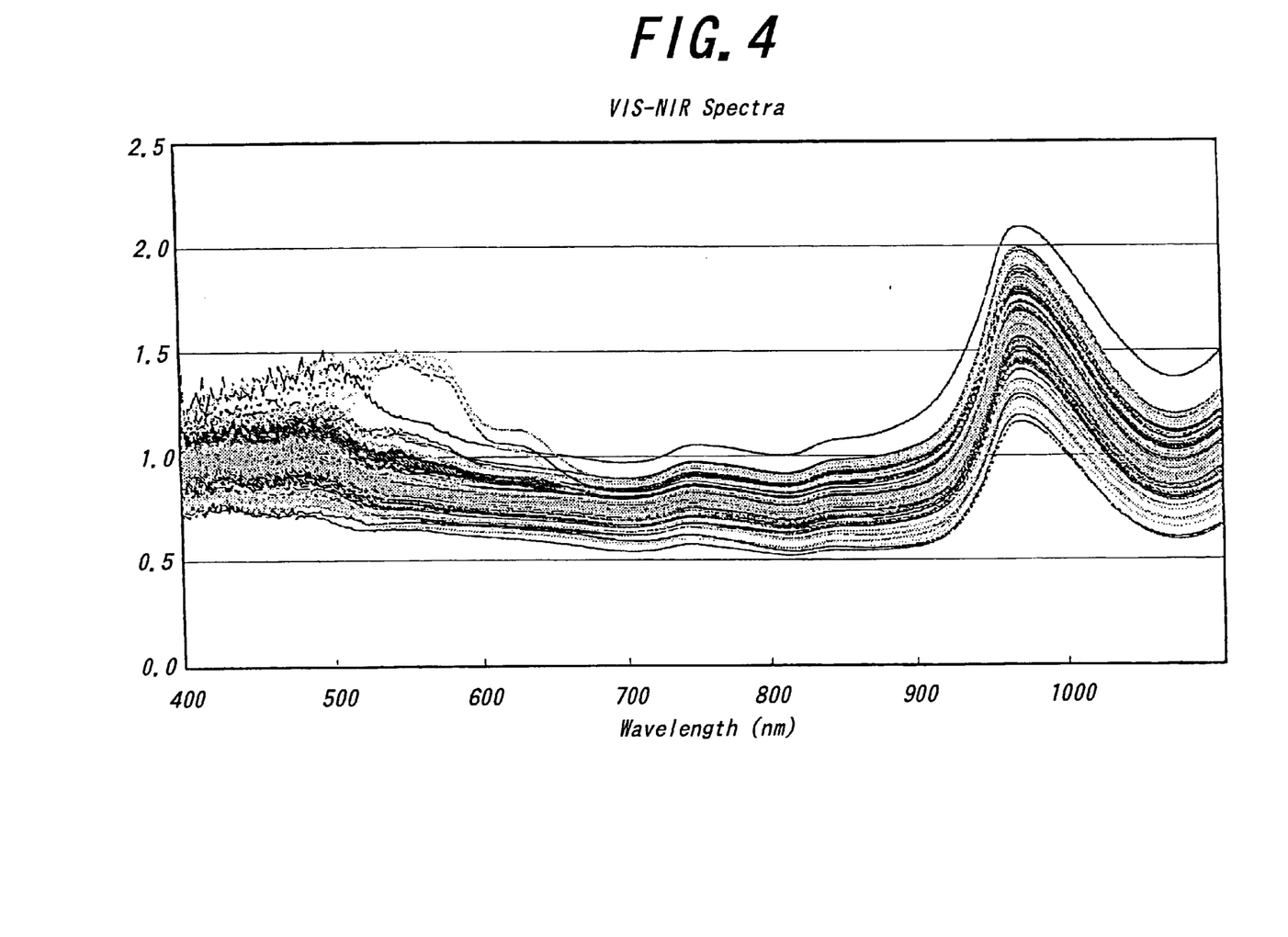
FIG. 4 is a graph showing an example of near infrared ray spectra of a number of raw milk samples in a wavelength range of 400 nm to 1100 nm.
Figure 5:
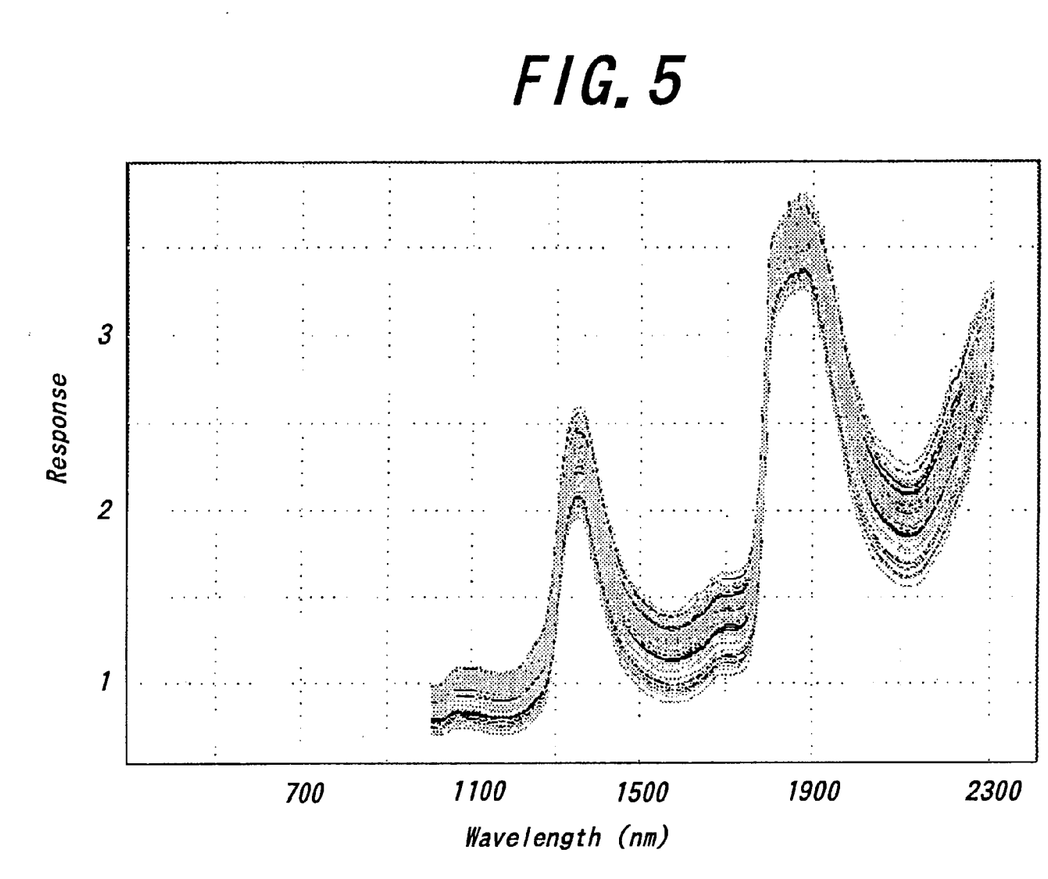
FIG. 5 is a graph showing an example of near infrared ray spectra of a number of raw milk samples in a wavelength range of 1100 nm to 2500 nm.

FIG. 4 is a graph showing an example of near infrared spectra of the raw milk wherein an ordinate gives absorbances represented by figures obtained by logarithmically converting reciprocals of light reflectances, and an abscissa denotes wavelengths (nm). A curve corresponds to an absorption spectra obtained by scanning over a wavelength of 400 nm to 1100 nm with use of the spectroscope 9 in FIG. 1. In FIG. 4, results obtained by measuring plural raw milk samples are displayed in an overlapped state. FIG. 5 is also a graph showing an example of near infrared spectra of the raw milk wherein an ordinate gives absorbances represented by figures obtained by logarithmically converting reciprocals of light reflectances, and an abscissa denotes wavelengths (nm). A curve corresponds to an absorption spectra obtained by scanning over a wavelength of 1100 nm to 2500 nm with use of the spectroscopy 9. In FIG. 5, results obtained by measuring plural raw milk samples are displayed, while overlapped.

All the curves are attributable to absorption spectra of water, and large peaks particularly near 1400 nm to 1500 nm and near 1850 nm to 2050 nm are attributable to molecular vibrations of water.

The above explanation is made on the transmission and reflection type construction where the light rays to be measured pass the sample SP, reflected at the inner surface of the sample container 41 and pass the sample SP again. In addition, measurement may be also made by a transmission type where the sample container 41 is made of a transparent material, and a transmitted lights having passed the sample SP are detected or a reflection type where the light rays reflected from the surface of the sample SP are measured.

The above explanation is made on the construction example where the spectroscope 9 is arranged between the light source 1 and the sample SP and the light rays to enter the sample SP are separated. In addition, a construction example may be used, where the spectroscope 9 is arranged between the sample SP and the light detector 20, and the transmitted light rays from the sample SP or the transmitted and reflected light rays are split.

Next, the multivariate regression analysis will be explained.

According to the multivariate regression method, relationship between a certain quantitative property of samples (corresponding to concentration or number of somatic cells in this application, for example) and one or more explanatory variants is established. In this application, the explanatory variable means a near infrared spectrum measured. However, the near infrared spectrum is actually constituted by not a single absorbance but absorbances at so many wavelengths. Therefore, the invention method in which the quantitative property (number of the somatic cells in this application) of the samples known from utterly different measurements are presumed by using near infrared spectra as multivariate data is a so-called multivariate regression analysis. In this application, the multivariate regression analysis is used to find out the relationship to the number of the somatic cells as the property to be presumed, based on the near infrared spectra as the multivariate data.

In the following, a PLS method (Partial Least Squares Regression) will be explained as one of the multivariate regression analyses (References: Tetsuro Aijima, "Chemometrics" published by Maruzen in 1991, and H. Martens & T. Naes, "Multivariate Calibration" published by John Willy, New York in 1991). As in FIG. 4, if scanning is effected at a resolution of 2 nm over a wavelength range of 700 nm to 1100 nm, 201 data are obtained per one scanning.

As a pretreatment for the spectra, a Kubelka-Munk conversion in which an apparent reflection index is converted to a ratio between an absorptivity $K(\lambda)$ and a scattering index $S(\lambda)$, a smoothing treatment such as moving average, a one- or two-dimensional differential treatment, a base line correction treatment or the like is effected, if necessary.

Figure 6:
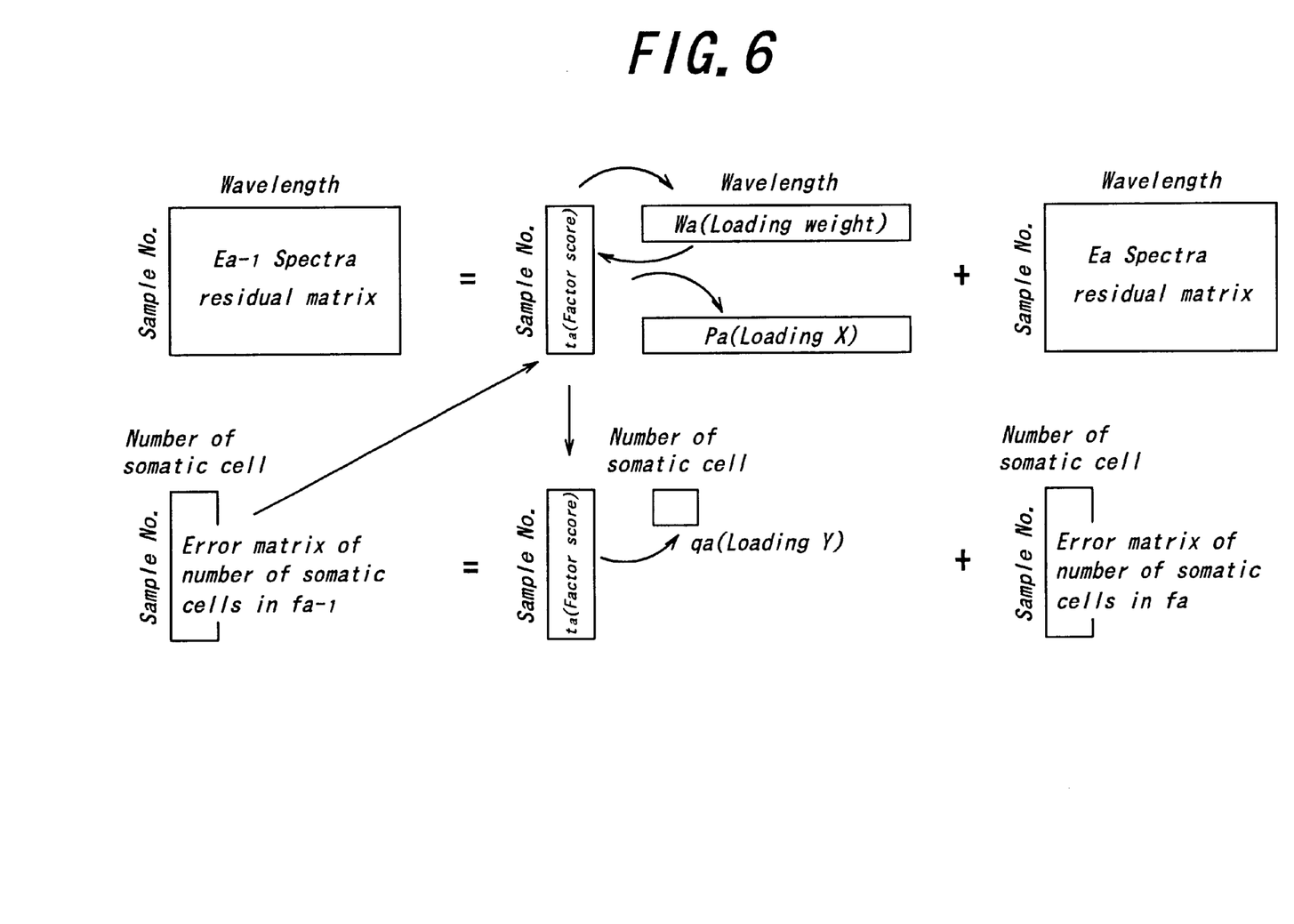
FIG. 6 is a figure for illustrating a procedure for performing a PLS method as one form of multivariate regression analyses according to the present invention.

FIG. 6 is an explanatory figure for illustrating a procedure for implementing the PLS method according to the present invention. An absorbance at one wavelength point is one-dimensional data constituted by plural components (somatic cells, proteins, lipids, etc. in the raw milk here or constituting components of the mammary gland), and one spectrum includes multi-dimensional data at M wavelength points in one scanning over the wavelengths. Therefore, one spectra data constitutes 1-dimensional data×M orthogonal coordinate spaces in the multivariate analysis of the somatic cells.

Next, variations in spectra data X and those in the number of somatic cells are represented by factor scores $t1, t2, t3, ---, ta, ---, th$ mutually orthogonal to one another with use of a orthogonal type PLS method. FIG. 6 shows a procedure for forming factor parameters of an a-th factor. E is a spectra residual matrix (matrix of number of wave-length data points×sampled number of samples), t a factor score, w a loading weight, and p and q X- and Y-loadings, respectively.

A spectra residual matrix $Ea-1$ for an $a-1$ factor is represented as a sum of a product between a factor score ta and a loading weight wa of the a-th factor, a product between a factor score ta and a X-loading, and the spectra residual matrix Ea of the a-th factor. An error matrix $fa-1$ of the somatic cells for the (a−1)th factor is represented by a sum of a product between the factor score ta and the Y-loading qa and an error matrix fa of the number of the somatic cells of the a-th factor.

Therefore, as an analysis procedure, the factor score ta, the loading weight wa, the X-loading pa and the Y-loading qa for the (a−1)th factor are calculated based on the spectra residue matrix $Ea-1$ and the somatic cell number error matrix $fa-1$ for the (a−1)th factor, and then the spectra residue matrix Ea and the somatic cell number error matrix fa are calculated.

More concretely, a first residual matrix $E0=X-Xm$ (Suffix m means "average value") of the spectra data and a first error matrix $f0=Y-Ym$ of the number of the somatic cells are calculated, and parameters t1, w1, p1 and q1 of the first factor are calculated. Then, a spectra residual matrix E1 and a somatic cell number error matrix f1 are newly formed by removing an influence of the first factor. Next, parameters t2, w2, p2 and q2 of the second factor are calculated by using the spectra residual matrix E1 and the somatic cell number error matrix f1. Then, a spectra residual matrix E2 and a somatic cell number error matrix f2 are newly formed by removing an influence of the second factor. Next, parameters t3, w3, p3 and q3 of the third factor are calculated by using the spectra residual matrix E2 and the somatic cell number error matrix f2. Then, a spectra residual matrix E3 and a somatic cell number error matrix f3 are newly formed by removing an influence of the third factor. Subsequently, calculations of parameters for each factor and formations of each of residual matrixes and error matrixes are repeated in the same manner consecutively until no effective factors are extracted.

Figure 7A:
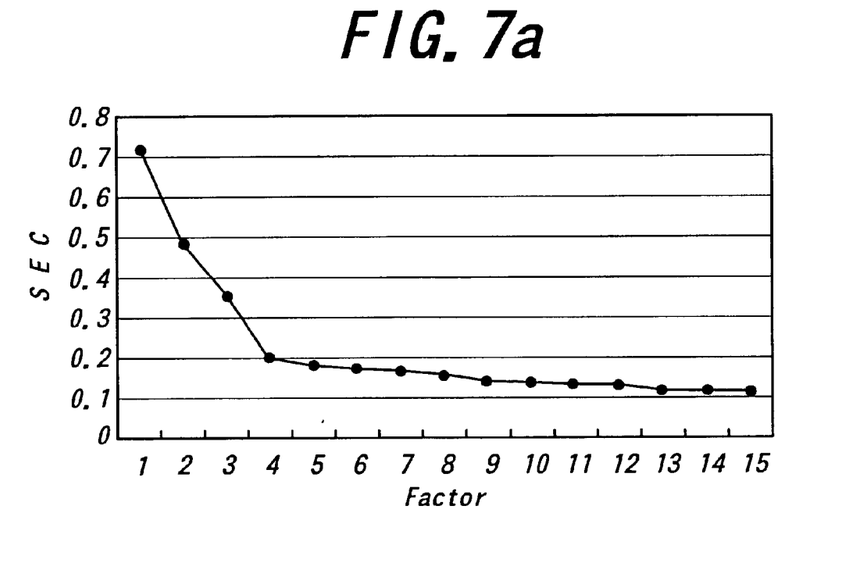
FIG. 7 gives graphs showing the number of PLS factors used in respective calculations and analysis errors.
Figure 7B:
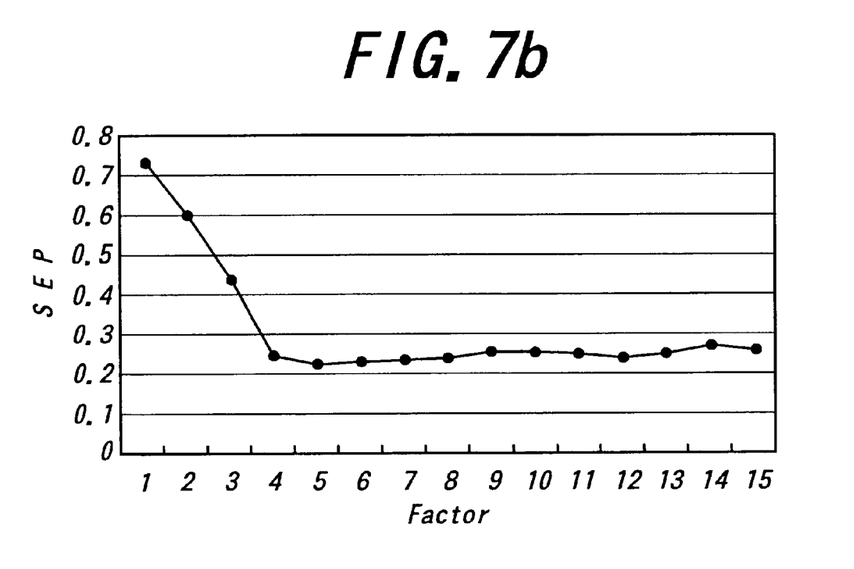

FIG. 7 gives graphs showing the number of PLS factors and analysis errors, which graphs are related to the number of the somatic cells. The ordinate gives the Log number of the somatic cells. FIG. 7(a) gives data (SEC: Standard Error of Calibration) obtained by measuring the number of the somatic cells when a sample having a known number of the somatic cells, and FIG. 7 gives data (SEP: Standard Error of Prediction) obtained by measuring the number of the somatic cells when a sample having an unknown number of the somatic cells was used.

From these graphs, it is seen that when the PLS factor is 5, that is, when error calculations are repeated until the 5th factor, both of the SEC value and the SEP value converge in an error range of about 0.25.

When the PLS factors up to the 5th one in FIG. 7 are used, a model which enables the number of the somatic cells to be calculated inversely from the near infrared spectra can be constructed. Therefore, a presumed number of somatic cells of a sample can be calculated by applying a near infrared spectrum related to the unknown number of the somatic cells to this model.

Figure 8:
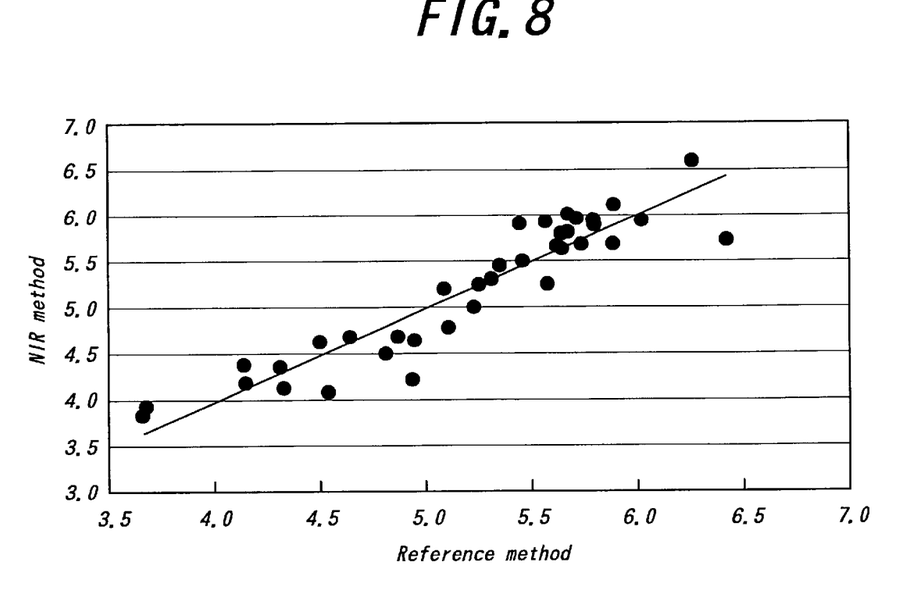
FIG. 8 is a graph showing the correlation between the number of somatic cells presumed by the PLS method and the actual number of the somatic cells when raw milk samples from cows were used.

FIG. 8 is a graph showing the correlation between a presumed number of somatic cells according to the PLS method and the actual number of the somatic cells. The abscissa gives the actual number of the somatic cells, and the ordinate the presumed number of the somatic cells. From this figure, it is seen that there is a strong correlation in that figures between both cases are distributed in an almost linear fashion. This shows that the multivariate analysis according to the PLS method is extremely effective.

Next, a MLR method and a PCR method will be described. According to the MLR method, a linear regression formula is constructed with respect to the number of somatic cells obtained in the measurement for a known sample by using only absorbances at plural specific wavelengths among new infrared spectra consisting of absorbances as multi-variations. An unknown number of somatic cells can be predicted by applying a near infrared spectrum for the unknown number of the somatic cells to be predicted to the thus constructed linear regression formula. In the PCR method, substantially the same calculation is effected as in the PLS method (Reference: Yoshikatu Miyashita & Sinichi Sasaki, "Kemometrix—Recognition and Multivariate analysis of chemical patterns" published by Kyoritsu Publisher in 1995).

Figure 9:
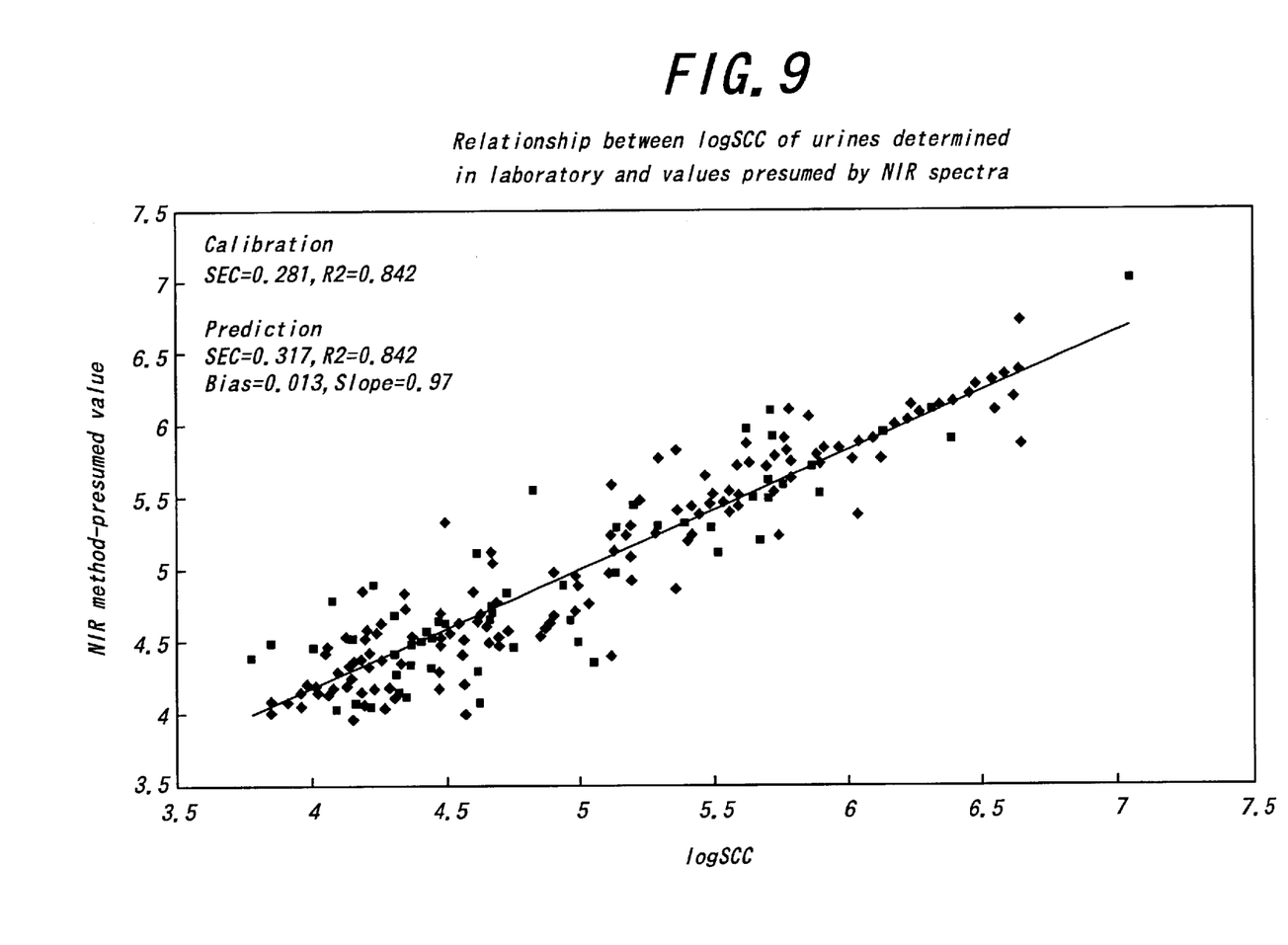
FIG. 9 is a graph showing the correlation between the number of somatic cells presumed by the PLS method and the actual number of the somatic cells when urine samples from cows were used.

FIG. 9 is a graph showing a correlation between a presumed number of somatic cells according to the PLS method and the actual one when urines of cows were used. Urine spectra were determined by the same measuring apparatus and the same measuring method as in the above raw milk spectra. From FIG. 9, it is seen that there is a strong correlation in that the actual numbers of the somatic cells in the abscissa and the presumed numbers of the somatic cells in the ordinate are distributed in an almost linear fashion. This shows that the multivariate analysis according to the PLS method is extremely effective.

EFFECTS OF THE INVENTION

As mentioned above in detail, according to the present invention, the number of the somatic cells can be measured by detecting the intensity of transmitted light rays, reflected light rays or transmitted and reflected light rays from urine, raw milk or mammary gland, and effecting the multivariate regression analysis of the obtained absorbance.

The number of the somatic cells can be readily measured at a high precision by the optical measurement of urine and data processing of the raw milk or the mammary gland.

What is claimed is:

1. A method for diagnosing whether a cow which is unknown to suffer from mastitis (hereinafter referred to as "unknown cow") suffers from mastitis or not, comprising the steps of:

irradiating visible light rays and/or near infrared rays in a wavelength range of 400 to 2500 nm into urine or a mammary gland of each of known healthy cows and known mastitic cows, detecting intensities of transmitted light rays, reflected light rays or transmitted and reflected light rays from said urine or mammary gland, determining the number of somatic cells for each of said known healthy and mastitic cows, and building up a model enabling an inverse calculation of the numbers of the somatic cells in the raw milk from the near infrared spectra by a multivariate regression analysis by using said detected intensities of the light rays and said detected numbers of the somatic cells;

irradiating visual light rays and/or near infrared rays in a wavelength range of 400 to 2500 nm into urine or a mammary gland of said unknown cow, detecting intensities of transmitted light rays, reflected light rays or transmitted and reflected light rays from said urine or mammary gland;

determining the number of the somatic cells for an unknown cow based on said detected intensities of the light rays for the unknown cow and said inverse calculation model; and determining whether the unknown cow suffers from mastitis or not, based on the determined number of the somatic cells.

2. A method for diagnosing mastitis of cows set forth in claim 1, wherein the urine or mammary gland is irradiated with near infrared rays in a wavelength range of 700 nm to 2500 nm.

3. A method for diagnosing mastitis of cows set forth in claim 1, wherein the urine or mammary gland is irradiated with near infrared rays in a wavelength range of 700 nm to 1100 nm or 1100 nm to 2500 nm.

4. The cow mastitis-diagnosing method set forth in any of claims 1, 2 and 3, wherein wavelengths of incident rays, transmitted light rays, reflected light rays or transmitted and reflected light rays from said urine or mammary gland are scanned, and wherein the multivariate regression analysis is applied to the thus obtained spectrum of the visual light rays and/or the near infrared rays.

5. The cow mastitis-diagnosing method set forth in claim 4, wherein the multivariate regression analysis is effected by multilinear regression (MLR), principal component regression (PCR) or partial least square regression (PLS).

6. The cow mastitis-diagnosing method set forth in any of claims 1, 2 and 3, wherein the multivariate regression analysis is effected by multilinear regression (MLR), principal component regression (PCR) or partial least square regression (PLS).

7. An apparatus for performing the method claimed in claim 1 for diagnosing whether a cow which is unknown to suffer from mastitis (hereinafter referred to as "unknown cow") suffers from mastitis or not, comprising:

an electromagnetic ray generator for generating visual light rays and/or near infrared rays in a wavelength range of 400 to 2500 nm;

an optical system for introducing the visual light rays and/or near infrared rays into urine or a mammary gland of a cow;

a detector for detecting an intensity of transmitted light rays, reflected light rays or transmitted and reflected light rays from said urine or mammary gland;

and a data processor which receives signals from said detector, and which builds and stores the model enabling the inverse calculation of the numbers of the somatic cells in the raw milk from the light spectra by the multivariate regression analysis by using said detected intensities of the light rays and said detected numbers of somatic cells.

8. The cow mastitis-diagnosing apparatus set forth in claim 7, wherein said electromagnetic ray generator is an infrared ray generator for generating near infrared rays in a wavelength range of 700 to 2500 nm, an infrared ray generator for generating near infrared rays in a wavelength range of 700 to 1100 nm, or an infrared ray generator for generating near infrared rays in a wavelength range of 1100 to 2500 nm.

9. The cow mastitis-diagnosing apparatus set forth in claim 7 or 8, which further comprises an optical fiber from said electromagnetic ray generator for introducing the visual light rays and/or near infrared rays into said urine or a mammary gland of the cow, and transmitted light rays, reflected light rays or transmitted and reflected light rays from said urine, or mammary gland is led to said detector through the optical fiber.

10. The cow mastitis-diagnosing apparatus set forth in claim 9, wherein the multivariate regression analysis is effected by multilinear regression (MLR), principal component regression (PCR) or partial least square regression (PLS).

11. The cow mastitis-diagnosing apparatus set forth in claim 7 or 8 wherein the multivariate regression analysis is effected by multilinear regression (MLR), principal component regression (PCP) or partial least square regression (PLS).

* * * * *